(12) United States Patent
Bobnock

(10) Patent No.: US 7,915,215 B2
(45) Date of Patent: Mar. 29, 2011

(54) FRAGRANCE-DELIVERY COMPOSITION COMPRISING BORON AND PERSULFATE ION-CROSSLINKED POLYVINYL ALCOHOL MICROCAPSULES AND METHOD OF USE THEREOF

(75) Inventor: Robert Stanley Bobnock, Menasha, WI (US)

(73) Assignee: Appleton Papers Inc., Appleton, WI (US)

( * ) Notice: Subject to any disclaimer, the term of this patent is extended or adjusted under 35 U.S.C. 154(b) by 121 days.

(21) Appl. No.: 12/289,010

(22) Filed: Oct. 17, 2008

(65) Prior Publication Data

US 2010/0099594 A1    Apr. 22, 2010

(51) Int. Cl.
*C11D 17/08* (2006.01)
(52) U.S. Cl. .............................. 510/418; 512/4
(58) Field of Classification Search .................. 510/418; 512/4
See application file for complete search history.

(56) References Cited

U.S. PATENT DOCUMENTS

| | | |
|---|---|---|
| 2,730,456 A | 1/1956 | Green et al. |
| 2,730,457 A | 1/1956 | Green et al. |
| 2,800,457 A | 7/1957 | Green |
| 2,800,458 A | 7/1957 | Green |
| 3,627,581 A | 12/1971 | Phillips, Jr. |
| 3,806,463 A | 4/1974 | Konishi et al. |
| 3,886,084 A | 5/1975 | Vassiliades |
| 3,996,405 A | 12/1976 | Porter, Jr. |
| 4,001,140 A | 1/1977 | Foris et al. |
| 4,027,065 A | 5/1977 | Brockett et al. |
| 4,089,802 A | 5/1978 | Foris et al. |
| 4,100,103 A | 7/1978 | Foris et al. |
| 4,105,823 A | 8/1978 | Hasler et al. |
| 4,130,299 A | 12/1978 | Wygant |
| 4,197,346 A | 4/1980 | Stevens |
| 4,244,836 A | 1/1981 | Frensch et al. |
| 4,269,729 A | 5/1981 | Maruyama |
| 4,287,074 A | 9/1981 | Earhart et al. |
| 4,318,818 A | 3/1982 | Letton et al. |
| 4,387,090 A | 6/1983 | Bolich, Jr. |
| 4,424,134 A | 1/1984 | Sissin et al. |
| 4,444,699 A | 4/1984 | Hayford |
| 4,446,042 A | 5/1984 | Leslie |
| 4,515,705 A | 5/1985 | Moeddel |
| 4,534,891 A | 8/1985 | Boden et al. |
| 4,537,706 A | 8/1985 | Severson, Jr. |
| 4,537,707 A | 8/1985 | Severson, Jr. |
| 4,550,862 A | 11/1985 | Barker et al. |
| 4,552,811 A | 11/1985 | Brown et al. |
| 4,561,998 A | 12/1985 | Wertz et al. |
| 4,597,898 A | 7/1986 | Vander Meer |
| 4,673,568 A | 6/1987 | Grollier et al. |
| 4,705,681 A | 11/1987 | Maes et al. |
| 4,714,562 A | 12/1987 | Roselle et al. |
| 4,767,547 A | 8/1988 | Staathof et al. |
| 4,898,781 A | 2/1990 | Onouchi et al. |
| 4,968,451 A | 11/1990 | Scheibel et al. |
| 5,064,650 A | 11/1991 | Lew |
| 5,085,857 A | 2/1992 | Reid et al. |
| 5,112,688 A | 5/1992 | Michael |
| 5,169,552 A | 12/1992 | Wise |
| 5,194,639 A | 3/1993 | Connor et al. |
| 5,225,117 A | 7/1993 | Matsushita |
| 5,246,603 A | 9/1993 | Tsaur et al. |
| 5,275,755 A | 1/1994 | Sebag et al. |
| 5,288,417 A | 2/1994 | Bauer et al. |
| 5,288,431 A | 2/1994 | Huber et al. |
| 5,364,634 A | 11/1994 | Lew |
| 5,403,499 A | 4/1995 | Kiefer et al. |
| 5,411,671 A | 5/1995 | Bauer et al. |
| 5,458,809 A | 10/1995 | Fredj et al. |
| 5,458,810 A | 10/1995 | Fredj et al. |
| 5,460,752 A | 10/1995 | Fredj et al. |
| 5,466,802 A | 11/1995 | Panandiker et al. |
| 5,470,507 A | 11/1995 | Fredj et al. |
| 5,545,340 A | 8/1996 | Wahl et al. |
| 5,545,350 A | 8/1996 | Baker et al. |
| 5,559,261 A | 9/1996 | Sivik |
| 5,562,849 A | 10/1996 | Wahl et al. |
| 5,565,145 A | 10/1996 | Watson et al. |
| 5,574,179 A | 11/1996 | Wahl et al. |
| 5,581,005 A | 12/1996 | Perkins |
| 5,597,936 A | 1/1997 | Perkins |
| 5,618,523 A | 4/1997 | Zysman et al. |

(Continued)

FOREIGN PATENT DOCUMENTS

GB    2062570 A    5/1981

(Continued)

OTHER PUBLICATIONS

Katz, David A., "Polyvinyl Alcohol Slime," 2005.

(Continued)

*Primary Examiner* — John R Hardee
(74) *Attorney, Agent, or Firm* — Muncy, Geissler, Olds & Lowe, PLLC

(57) ABSTRACT

An aqueous composition is provided having a pH of from about 2.0 to about 5.7 to about 12.8 and comprising boron or persulfate ion-crosslinked polyvinyl alcohol microcapsules. A method of delivering a fragrance to a substrate is further provided comprising applying to the substrate an aqueous composition comprised of fragrance-containing, boron or persulfate ion-crosslinked, polyvinyl alcohol microcapsules, as well as a method of cleaning a substrate comprising applying to the substrate an aqueous composition comprised of fragrance-containing, boron or persulfate ion-crosslinked, polyvinyl alcohol microcapsules together with at least one cleaning component.

37 Claims, No Drawings

U.S. PATENT DOCUMENTS

| | | |
|---|---|---|
| 5,661,118 A | 8/1997 | Cauwet et al. |
| 5,674,832 A | 10/1997 | Keys |
| 5,679,630 A | 10/1997 | Baeck et al. |
| 5,703,030 A | 12/1997 | Perkins et al. |
| 5,703,034 A | 12/1997 | Offshack et al. |
| 5,705,464 A | 1/1998 | Scheper et al. |
| 5,731,278 A | 3/1998 | Nair et al. |
| 5,756,436 A | 5/1998 | Royce et al. |
| 5,759,990 A | 6/1998 | Wahl et al. |
| 5,776,443 A | 7/1998 | Vinski et al. |
| 5,837,661 A | 11/1998 | Evans et al. |
| 5,877,145 A | 3/1999 | Wahl et al. |
| 5,902,781 A | 5/1999 | Painter |
| 5,914,307 A | 6/1999 | DeNome et al. |
| 5,916,862 A | 6/1999 | Morelli et al. |
| 5,929,022 A | 7/1999 | Velazquez |
| 5,932,203 A | 8/1999 | Coffindaffer et al. |
| 5,935,561 A | 8/1999 | Inman et al. |
| 5,939,373 A | 8/1999 | Haeggberg et al. |
| 5,962,386 A | 10/1999 | Scheper et al. |
| 5,968,286 A | 10/1999 | Crudele et al. |
| 5,968,881 A | 10/1999 | Haeggberg et al. |
| 5,990,065 A | 11/1999 | Vinson et al. |
| 6,017,871 A | 1/2000 | Baeck et al. |
| 6,020,294 A | 2/2000 | Getty et al. |
| 6,069,122 A | 5/2000 | Vinson et al. |
| 6,143,707 A | 11/2000 | Trinh et al. |
| 6,162,423 A | 12/2000 | Sebag et al. |
| 6,335,315 B1 | 1/2002 | Trinh et al. |
| 6,936,580 B2 | 8/2005 | Sherry et al. |
| 7,082,951 B2 | 8/2006 | Barnabas |
| 7,163,349 B2 | 1/2007 | Policicchio et al. |
| 7,199,094 B2 | 4/2007 | Cheung et al. |
| 2004/0115091 A1 | 6/2004 | Beerling et al. |
| 2006/0051425 A1 | 3/2006 | Kvitnitsky et al. |
| 2006/0248665 A1 | 11/2006 | Pluyter et al. |
| 2007/0004610 A1 | 1/2007 | Brain et al. |
| 2007/0149424 A1 | 6/2007 | Warr et al. |
| 2007/0207174 A1 | 9/2007 | Pluyter et al. |
| 2008/0038301 A1 | 2/2008 | Ueda |
| 2008/0038302 A1 | 2/2008 | Tanaka |
| 2008/0176781 A1 | 7/2008 | Fadel et al. |
| 2010/0099566 A1* | 4/2010 | Bobnock ..................... 504/187 |

FOREIGN PATENT DOCUMENTS

| | | |
|---|---|---|
| WO | WO-00/37117 | 6/2000 |

OTHER PUBLICATIONS

Calanese, "Celvol Polyvinyl Alcohol Product Line," pp. 3-7.

* cited by examiner

FRAGRANCE-DELIVERY COMPOSITION COMPRISING BORON AND PERSULFATE ION-CROSSLINKED POLYVINYL ALCOHOL MICROCAPSULES AND METHOD OF USE THEREOF

BACKGROUND OF THE INVENTION

The present invention is directed to a fragrance-delivery composition comprising boron or persulfate ion-crosslinked polyvinyl alcohol microcapsules and a method of use thereof. Microcapsules have been known for many years and have many and varied uses. For instance, microcapsules have utility in the areas of carbonless paper, pressure sensitive adhesives, pressure sensitive indicators, and fragrance delivery compositions.

Many processes for microencapsulation are known. These include methods for capsule formation such as described in U.S. Pat. Nos. 2,730,456, 2,800,457; and 2,800,458. Other useful methods for microcapsule manufacture are include those described in U.S. Pat. Nos. 4,001,140; 4,081,376 and 4,089,802 describing a reaction between urea and formaldehyde; U.S. Pat. No. 4,100,103 describing reaction between melamine and formaldehyde; and British Patent No. 2,062,570 describing a process for producing microcapsules having walls produced by polymerization of melamine and formaldehyde in the presence of a styrenesulfonic acid. Microencapsulation is also taught in U.S. Pat. Nos. 2,730,457 and 4,197,346. Processes for forming microcapsules from urea-formaldehyde resin and/or melamine formaldehyde resin are disclosed in U.S. Pat. Nos. 4,001,140, 4,081,376; 4,089,802; 4,100,103; 4,105,823; 4,444,699. Alkyl acrylate-acrylic acid copolymer capsules are taught in U.S. Pat. No. 4,552,811.

Common microencapsulation processes can be viewed as a series of steps. First, the core material which is to be encapsulated is emulsified or dispersed in a suitable dispersion medium. This medium is preferably aqueous but involves the formation of a polymer rich phase. Frequently, this medium is a solution of the intended capsule wall material. The wall material is thereby contained in the liquid phase which is also dispersed in the same medium as the intended capsule core material. The liquid wall material phase deposits itself as a continuous coating about the dispersed droplets of the internal phase or capsule core material. The wall material is then solidified. This process is commonly known as coacervation.

Phase separation processes, or coacervation processes are described in U.S. Pat. Nos. 2,800,457 and 2,800,458. Encapsulations based on polymerization of urea and formaldehyde, monomeric or low molecular weight polymers of dimethylol urea or methylated dimethylol urea, melamine and formaldehyde, methylated melamine formaldehyde, monomeric or low molecular weight polymers of methylol melamine or methylated methylol melamine, are taught in U.S. Pat. No. 4,552,811. These materials are typically dispersed in an aqueous vehicle and the reaction is conducted in the presence of acrylic acid-alkyl acrylate copolymers.

Polyvinyl alcohol microcapsules are taught by U.S. Pat. Nos. 3,886,084; 4,244,836; 4,269,729; 4,898,781; 5,064,650; 5,225,117; and 5,246,603.

In addition, core-material microcapsules have been used for many years in a variety of compositions, including but not limited to cleaning compositions. Perfume-containing microcapsules have also been used for many years in compositions designed to counteract malodors. Such microcapsules may contain a variety of cleaning solution-compatible components, such as cleaning oils, fragrances, colorants, etc. For instance, when used in hard surface cleaners such as floor cleaners, such microcapsules typically are intended to be subjected to crushing or disintegrating force upon application to a substrate to permit release of the core material, such as a fragrant oil.

A disadvantage with respect to the use of prior art microcapsules produced by the above methods in, for example, the imparting of a fragrance during the cleaning of hard surfaces is that the microcapsules are somewhat resistant to rupture. As a result, the deposition of such microcapsules (which include a fragrant core material) is less than effective, as the microcapsules do not rupture absent physical force being applied. The microcapsules can also migrate into the pores of any porous surfaces to which the cleaning product is applied so as to further resist rupture.

U.S. Pat. No. 5,064,650 discloses salt-sensitive microcapsules. U.S. Pat. No. 5,364,634 discloses pH sensitive microcapsules. U.S. patent publication 2004/0115091 discloses perfume-containing microcapsules which are ruptured by the application of physical force.

It is thus desirable to provide a method for the formation of microcapsules which are susceptible to rupture or disintegration in the absence of applied force under the desired conditions of use.

It is further desirable to provide an aqueous cleaning solution containing microcapsules that can be used with advantage wherein microcapsules contained therein are susceptible to rupture or disintegration in the absence of applied force under the desired conditions of use.

It is further desirable to provide a method of cleaning or fragrance-delivery comprising the use of a solution containing the fragrance-containing microcapsules of the present invention which are susceptible to rupture or disintegration in the absence of applied force under the desired conditions of use.

OBJECTS AND SUMMARY OF THE INVENTION

It is accordingly an object of the present invention to provide microcapsules which are particularly useful as a core component delivery system in an aqueous cleaning or fragrance-delivery composition.

It is also an object of the present invention to provide microcapsules having particular utility in aqueous compositions such as cleaning or fragrance delivery compositions.

It is still yet further an object of the present invention to provide a method of cleaning or fragrance delivery using the novel cleaning and/or fragrance-delivery composition of the present invention.

In accordance with the present invention, there is thus provided a water-containing composition having a pH of from about 4.8 to about 12.8 or even from 1.9 to 12.8 and comprising boron or persulfate ion-crosslinked polyvinyl alcohol microcapsules.

In accordance with the present invention, there is also provided a method of cleaning a substrate, comprising applying a cleaning composition to the substrate comprising an aqueous cleaning composition having a pH of from about 6 to about 12 and comprising an effective amount of at least one cleaning component and boron ion-crosslinked fragrance-containing polyvinyl alcohol microcapsules.

In still further in accordance with the present invention, there is provided a method of delivering a fragrance to a substrate, comprising applying to the substrate an aqueous composition comprised of fragrance-containing, boron ion-crosslinked, polyvinyl alcohol microcapsules, the microcapsules being temperature-sensitive and susceptible to disintegration in the absence of the application of crushing force upon drying of the composition subsequent to application of the composition to the substrate.

In accordance with a preferred embodiment of the present invention, the microcapsules of the present invention are prepared by a method comprising the steps of:

(a) providing an aqueous suspension of polyvinyl alcohol having a solids content within the range of about 4 to about 25% by weight;

(b) combining the aqueous suspension of step (a) with at least one emulsifiable fragrance component under sufficient applied shear and for a time sufficient to obtain a stable emulsion of the at least one emulsifiable fragrance component in the aqueous suspension of polyvinyl alcohol; and (c) subsequently adding a source of boron or persulfate ions to the emulsion of step (b) in an amount and under conditions sufficient to cross-link the polyvinyl alcohol to obtain an aqueous mixture of fragrance-containing microcapsules.

DETAILED DESCRIPTION OF THE INVENTION

The novel cleaning and/or fragrance-delivery composition of the present invention comprises an aqueous composition comprising boron ion-crosslinked polyvinyl alcohol-based fragrance-containing microcapsules having desirable thermal, salinity and pH sensitivity.

The microcapsules of the present invention are formed by a coacervation method where polyvinyl alcohol is deposited around droplets of an emulsifiable fragrance component in aqueous suspension, with the polyvinyl alcohol subsequently being crosslinked by boron or persulfate ions.

Internal phase oils, or oil phase, or oil solvent or organic solvents, or "nonsolvent for the water phase," are used interchangeably for purposes hereof. An organic solvent can optionally be used with the perfume core material. Where the perfume core material is itself an essential oil or nonsolvent for the water phase, additional organic solvent becomes optional. Typical organic solvents that can optionally be employed together with the perfume core material, are typically preferably a nonsolvent for the water phase, and are used in an amount sufficient for emulsifying the perfume core material, and may include various solvents such as mono-propylene glycol mono-propyl ether, di-propylene glycol mono-propyl ether, mono-propylene glycol mono-butyl ether, di-propylene glycol mono-propyl ether, di-propylene glycol mono-butyl ether; tri-propylene glycol mono-butyl ether; ethylene glycol mono-butyl ether; di-ethylene glycol mono-butyl ether, ethylene glycol mono-hexyl ether and di-ethylene glycol mono-hexyl ether, 3-methoxy-3-methyl-butanol, alkanediols, propylene glycols, various alcohols, essential oils, and blends of any of the foregoing with alcohols or various diluents. Common diluents or organic solvents or co-solvents include ethanol, isopropanol, diethylene glycol, monoethyl ether, dipropylene glycol, diethyl phthalate, tri-ethyl citrate, isopropyl myristate, etc. The solvent for the core material and the perfume core material is each independently selected to be somewhat or substantially water insoluble or water insoluble to a degree or able to be made substantially water insoluble at certain pH's. The purpose of the organic solvent is to facilitate emulsifying the core material by solubilizing or dispersing the desired perfume core material and/or partitioning the perfume core material from the water in the capsule formation process. Other useful optional solvents for the core include vegetable oils such as canola oil, soybean oil, corn oil, cottonseed oil, alkyl esters of fatty acids, transesterified vegetable oils such as transesterified canola oil, soybean oil, corn oil, cottonseed oil, sunflower oil, methyl ester of oleic acid, paraffinic aliphatic hydrocarbons The liquid core material or solvent for the perfume core material employed in the microcapsules can be any material which is liquid within the temperature range at which the capsules are formed. Examples of eligible organic solvent liquids also include, but are not limited to various conventional organic solvents including ethyldiphenylmethane (U.S. Pat. No. 3,996,405); benzylxylene (U.S. Pat. No. 4,130,299); alkyl biphenyls such as propylbiphenyl (U.S. Pat. No. 3,627,5810; butylbiphenyl (U.S. Pat. No. 4,287,074); dialkyl phthalates in which the alkyl groups thereof have from 4 to 13 carbon atoms, e.g. dibutyl phthalate, dioctylphthalate, dinonyl phthalate and ditridecylphthalate; 2,2,4-trimethyl-1,3-pentanediol diisobutyrate (U.S. Pat. No. 4,027,065); $C_{10}$-$C_{14}$ alkyl benzenes such as dodecyl benzene; alkyl or aralkyl benzoates such as benzyl benzoate; alkylated naphthalenes such as dipropylnaphthalene (U.S. Pat. No. 3,806,463); partially hydrogenated terphenyls; high-boiling straight or branched chain hydrocarbons; and mixtures of the above. The solvents for the perfume core material can include any of the above or the like which possess sufficient solubility for the perfume core material. Common diluents such as straight chain hydrocarbons can also be blended with any of the solvents, or blend of solvents. The solvent is selected on the basis of hydrophobicity and ability to disperse or solvate the perfume core material. The internal phase oil ends up as the core or internal contents of the microcapsule along with the perfume core material.

In an alternate aspect the perfume core material can be a fraction of the microcapsule core or 100 weight percent of the core such as when the core is selected to be an essential oil, rather than an optional additional solvent. When the perfume core material is itself an organic liquid, additional solvent or diluent can be optional depending on the desired amount of fragrance sought to be delivered by the delivery system of the invention. The weight percent of the perfume core material from 0.0001 to 100 weight percent, plus diluent as needed, as the internal phase of the microcapsules is selected to be sufficient to provide the desired fragrance strength or effect and is readily determinable by the skilled artisan. For cost constraints often the perfume of the perfume core material is preferred to be kept at a level of from 0% to 10%, or even from 0% to 35%, preferably from 0.1% to 5%, and more preferably from 0.2% to 7%, or even from 0.2% to 3% by weight of the perfume core material, though from a technical standpoint higher loadings are readily able to be accomplished in the invention if desired.

More specifically, a stable emulsion of polyvinyl alcohol and at least one emulsifiable fragrance component (such as a fragrant oil) or perfume core material is formed, followed by the step of contacting the stable emulsion with a source of boron or persulfate ions to crosslink the polyvinyl alcohol to form a suspension of the desired polyvinyl alcohol-based microcapsules having a fragrant core material.

The advantages of the present invention are many. For instance, it has been unexpectedly and desirably found that the microcapsules produced by the method of the present invention exhibit thermal and/or pH sensitivity. Such thermal and/or pH sensitivity enables the microcapsules to disintegrate and release the fragrant core material contained therein under destabilizing conditions of temperature and/or pH. The microcapsules can be caused to rupture by changing the salinity of the solution to which they are exposed, or by changing the pH of the solution (such as by contact with skin). Little or no heat is required to produce the microcapsules. The use of polyvinyl alcohol is also an advantage in that it serves both as an emulsifier, and as a wall material for the microcapsule, thus avoiding the need for the use of separate emulsifiers and encapsulating materials. Milling (or stirring) times are also greatly shortened to 5 minutes or less. Further, the microcapsules of the present invention disperse readily in either cationic or anionic systems.

That is, such microcapsules, once removed from the aqueous medium in which they are formed and in which they exhibit relative structural stability under ambient conditions and a pH of from 4.0 to 13, or even from 2 to about 13 are particularly susceptible to changes in temperature and/or pH such that, upon exposure to same, readily rupture or disintegrate and release the content of the microcapsule. As discussed in greater detail below, such microcapsules have particular utility in cleaning products for hard surfaces where the microcapsules rupture and/or degrade subsequent to application and the fragrant core material is released, as well as in applications where it is desired to apply a fragrant component to a substrate.

In the present invention, the fragrant core material is enclosed by a polyvinyl alcohol coating material.

Polyvinyl alcohol and its derivatives used in this invention include completely saponified polyvinyl alcohol, partially saponified polyvinyl alcohol, anion-modified polyvinyl alcohol, and the like. The use of polyvinyl alcohol as a core coating material in the formation of microcapsules is known to those skilled in the art. See the previously-mentioned U.S. Pat. Nos. 3,886,084; 4,244,836; 4,269,729; 4,898,781; 5,064,650; 5,225,117; and 5,246,603, among others.

Various modified polyvinyl alcohols can also be used as the coating material. Examples of such modified polyvinyl alcohols which are advantageously usable in this invention include, but are not limited to, cation modified polyvinyl alcohols obtained by the treatment with, for example, dimethyl aminopropyl acrylamide and methyl chloride; alkyl modified polyvinyl alcohols obtained by the treatment with, for example, vinyl versatate (VEOVA); acid modified polyvinyl alcohols obtained by the treatment with, for example, acrylic acid or itaconic acid; and acetacetylated modified polyvinyl alcohols using, for example, diketenes.

Suitable polyvinyl alcohol polymers which can be used in the present invention include those containing not less than 60 mol % total of vinyl alcohol units and vinyl acetate units and having a cloud point when formulated into aqueous solutions. For example, suitable polymers include partially saponified polyvinyl alcohols having saponification degrees of 60 to 80 mol %; completely or partially saponified, modified polyvinyl alcohols obtained by the introduction of 0.1 to 20 mol % of ethylene and/or an olefin having a long chain alkyl group of 3 to 20 carbon atoms into the polymer by copolymerization and/or by modification of the polymer after the polymerization reaction; partially saponified, modified polyvinyl alcohols obtained by introduction of 0.1 to 5 mol % of a hydrophilic group into the polymer by copolymerization; partially or completely saponified, modified polyvinyl alcohols obtained by the introduction of 0.1 to 20 mol % of a hydrophilic group and 0.1 to 20 mol % of ethylene and/or an olefin having a long chain alkyl group of 3 to 20 carbon atoms into the polymer by copolymerization and/or by modification of the polymer after the polymerization reaction; partially or completely saponified polyvinyl alcohols having a lactone ring content of 1 to 40 mol %; etc.

These polyvinyl alcohol polymers can be prepared by: (1) polymerizing vinyl acetate alone, followed by saponification; (2) copolymerizing vinyl acetate with at least one comonomer selected from the group of ethylene, olefinically unsaturated compounds each having a long chain alkyl group and olefinically unsaturated, hydrophilic-group-containing compounds, followed by saponification; (3) polymerizing vinyl acetate alone or copolymerizing vinyl acetate with an olefinically unsaturated compound having a hydrophilic group, followed by saponification and by subsequent acetalization, esterification and/or etherification with an aldehyde, acid and/or alcohol each having a long chain alkyl group; (4) copolymerizing vinyl acetate with an olefinically unsaturated compound having a carboxyl or carboxylate ester group, followed by saponification and by subsequent acid or heat treatment, and other methods.

Suitable examples of olefinically unsaturated compounds which have a long chain alkyl group are alpha olefins such as 1-octadecene, 1-hexadecene, 1-dodecene and 1-octene; vinyl esters such as vinyl stearate, vinyl laurate, vinyl versatate and vinyl propionate; acrylate esters such as stearyl acrylate, lauryl acrylate, octyl acrylate and butyl acrylate; methacrylate esters such as stearyl methacrylate, lauryl methacrylate, octyl methacrylate and butyl methacrylate; vinyl ethers such as stearyl vinyl ether, lauryl vinyl ether and butyl vinyl ether, and similar compounds having a long chain alkyl group of 3-20 carbon atoms in the side chain.

Suitable examples of olefinically unsaturated compounds having a hydrophilic group are, for example, carboxyl-containing compounds such as acrylic acid, methacrylic acid, maleic acid, maleic anhydride, itaconic acid and fumaric acid and esters thereof; sulfonic acid compounds such as vinylsulfonic acid and allylsulfonic acid, esters and alkali metal salts thereof; and nitrogen-containing compounds such as vinylpyrrolidone, acrylamide, N-substituted acrylamides and vinyl pyridine.

Suitable examples of the above described olefinically unsaturated compounds having a carboxyl or carboxylate ester group include acrylic acid, methacrylic acid, maleic acid, maleic anhydride, itaconic acid and fumaric acid, and esters thereof.

Suitable examples of aldehydes, acids, and alcohols which have a long chain alkyl group for use in the modification of the vinyl polymer after polymerization include stearic acid, stearylaldehyde, stearyl alcohol, lauric acid, laurylaldehyde, lauryl alcohol, butyric acid, butyraldehyde, butanol, etc.

A number of polyvinyl alcohol polymers suitable for use in the present invention are commercially available, such as partially hydrolyzed Celvol 523, 502, 205, 203 and 540.

The specific temperatures used in the microencapsulation process are determined by the varying properties of the polyvinyl alcohol polymer used and/or by variations in the concentration of the polyvinyl alcohol polymer in the aqueous solution. Generally. however, a temperature within the range of from about 20 to about 65° C. or even to about 85° C. is employed during the crosslinking process. One advantage of the present invention is that the crosslinking process may occur under ambient conditions in the absence of added heat input, while also occurring under a period of time less than what would normally be expected.

The pH of the solution during crosslinking is generally maintained within the range of from about 4 to about 10 or even from 2 to about 10. It has been found that the resulting boron or persulfate ion-crosslinked polyvinyl alcohol microcapsules are relatively stable under such conditions of temperature and pH.

In the present invention, the concentration of the polyvinyl alcohol polymer in the aqueous solution is generally maintained within the range of 3 to 25 weight % at the time of phase separation. It is also possible, however, (1) to use an aqueous solution of greater polyvinyl alcohol polymer concentration in the dispersion step to increase the efficiency of this step and then adjust the concentration to the desired level by dilution of the solution, or (2) to use a more dilute aqueous polyvinyl alcohol polymer solution in the dispersion step and then adjust the concentration in the phase separation step upward by gradually adding a concentrated aqueous solution of the polyvinyl alcohol polymer to the dilute solution.

With regard to the method employed for treating the wall membranes of the capsules to solidify the same, a boron or persulfate ion is used which is capable of reacting with the polyvinyl alcohol polymer which results in substantial crosslinking/solidification of the separated phase of the polyvinyl alcohol polymer in the aqueous emulsion. Suitable boron ion-sources include boric acid and borates such as Borax, ulexite, colemanite, sodium tetraborate, sodium metaborate, calcium borate disodium tetraborate peutahydrate, disodium tetraborate decahydrate, disodium tetraborate sodium metaborate, sodium perborate, and perborate silicate. The term "borate" includes salts or esters of boric acid and includes any compound possessing a borate group which is capable of complexing with the polyvinyl alcohol emulsifying agent in solution to form an impermeable coating. The walls of the microcapsules of the present invention are formed of non-metallic bonds. Boron is considered to be a non-metallic element as defined in The Van Nostrand Chemist's Dictionary, D. Van Nostrand Company, Inc., (1953).

The persulfate ion source can include various peroxy monosulfates and peroxydisulfates. More particularly the persulfate ion source can include alkali peroxymonosulfates, alkali peroxydisulfates, ammonium peroxydisulfates. A common alkali peroxydisulfate is potassium persulfate also known as dipotossium persulfate or potassium peroxydisulfate. Sodium persulfate is also useful and is also known as sodium peroxydisulfate and disodium peroxydisulfate.

The crosslinking or complexing boron or persulfate-containing agent is utilized in amounts sufficient to result in the formation of microcapsules. The relative amounts vary with the particular system, and may be easily determined in each case. The polyvinyl alcohol emulsifying agent is dual functional, and serves not only as an emulsifying agent, i.e., to stabilize the surface of the emulsifiable fragrance component and prevent coalescense, but actually provides the shell. Thus, the polyvinyl alcohol emulsifying agent should be provided in relatively substantial amounts of, for example, at least about 0.5 part by weight per part of boron ion crosslinking or complexing agent. Suitable amounts include, for example, between about one and about 100 parts of polyvinyl alcohol, preferably between about one and about 20 parts polyvinyl alcohol, per part by weight of boron ion crosslinking or complexing agent.

A variety of perfume core components may be employed with advantage in the present invention, the selection of which is well within the ability of one skilled in the art. The terms perfume core materials and perfume core components are used interchangeably for purposes of the invention. Suitable components include those capable of being emulsified and encapsulated by the polyvinyl alcohol polymer of the present invention, and which are either totally or at least substantially insoluble in water in order to permit the requisite emulsion to be formed.

A perfume material suitable for use in the present invention is defined as being any material having an odor that is either pleasant or masking in character, which acts to counteract any malodor that may be encountered, and which may be incorporated into the microcapsule of the present invention by means of the method of encapsulation of the present invention. It is preferred that the perfume material that is used have the ability to counteract or neutralize a malodor, as opposed to merely mask the malodor.

For instance, exemplary perfume core components are disclosed in WO 00/37117; U.S. Pat. Nos. 4,534,891; 5,112,688; and 5,145,842; as well as published application Nos. 2004/0115091; 2006/0248665; 2007/0004610; and 2007/0207174, each herein incorporated by reference.

Such perfume materials may comprise, without limitation, subject to the criteria above, extracts, essential oils, absolutes, resinoids, resins, hydrocarbons, alcohols, aldehydes, ketones, ethers, acids, esters, acetals, ketals, nitriles, etc.

Examples of perfume core materials which can be used in the invention include but are not limited to geraniol, geranyl acetate, linalol, linalyl acetate, tetrahydrolinalol, citronellol, citronellyl acetate, dihydromyrcenol, dihydromyrcenyl acetate, tetrahydromyrcenol, terpineol, terpinyl acetate, nonpol, nopyl acetate, 2-phenyl-ethanol, 2-phenylethyl acetate, benzyl alcohol, benzyl acetate, benzyl salicylate, styrallyl acetate, benzyl benzoate, amyl salicylate, dimethylbenzyl-carbinol, trichloromethylphenyl-carbinyl acetate, p-tert-butylcyclohexyl acetate, isononyl acetate, vetiveryl acetate, vetiverol, .alpha.-hexylcinnamaldehy-de, 2-methyl-3-(p-tert-butylpheyl)propanal, 2-methyl-3-(p-isopropylphenyl)-propanal, 2-(p-tert-butylpheyl)-propanal, 2,4 diethyl-cyclohex-3-enyl-carb-oxaldehyde, tricyclodecenyl acetate, tricyclodecenyl propionate, 4-(4-hydroxy-4-methylpentyl)-3-cyclohexenecarboxyaldehyde, 4-(4-methyl-3-pentenyl)-3-cyclohexenecarboxaldehyde, 4-acetoxy-3-pentyl-tetrahydropyran, 3-carboxymethyl-2-pentylcyclopentane, 2-n-heptylcyclopentanone, 3-methyl-2-pentyl-2-cyclopentenone, n-decanal, n-dodecanal, 9-decenol-1, phenoxyethyl isobutyrate, phenylacetaldehyde dimethyl-acetal, phenylacetaldehyde diethylacetal, geranyl nitrile, citronellyl nitrile, cedryl acetate, 3-isocamphylcyclohexanol, cedryl methyl ether, isolongifolanone, aubepine nitrile, aubepine, heliotropin, coumarin, eugenol, vanillin, diphenyl oxide, hydroxycitronellal, ionones, methylionones, isomethylionones, irones, cis-3-hexenol and esters thereof, indan musks, tetralin musks, isochroman musks, macrocyclic ketones, macrolactone musks, ethylene brassylate, etc.

Examples of essential oils useful as perfume core materials include but are not limited to angelica root oil, anise oil, arnica blossom oil, basil oil, bay oil, bergamot oil, champaca blossom oil, noble fir oil, noble fir cone oil, elemi oil, eucalyptus oil, fennel oil, spruce needle oil, galbanum oil, geranium oil, ginger grass oil, guaiacwood oil, gurjun balsam oil, helichrysum oil, ho oil, ginger oil, iris oil, cajeput oil, calamus oil, camomile oil, camphor oil, canaga oil, cardamom oil, cassia oil, pine needle oil, copaiva balsam oil, coriander oil, spearmint oil, caraway oil, cumin oil, lavender oil, lemon grass oil, lime oil, mandarin oil, balm oil, musk seed oil, myrrh oil, clove oil, neroli oil, niaouli oil, olibanum oil, orange oil, origanum oil, palmarosa oil, patchouli oil, peru balsam oil, petitgrain oil, pepper oil, peppermint oil, pimento oil, pine oil, rose oil, rosemary oil, sandalwood oil, celery oil, spike oil, star anise oil, turpentine oil, thuja oil, thyme oil, verbena oil, vetiver oil, juniperberry oil, wormwood oil, wintergreen oil, ylang-ylang oil, hyssop oil, cinnamon oil, cinnamon leaf oil, citronella, lemon oil and cypress oil. Other useful perfume core materials can include oil or solvent dispersions or oil dispersions of ambrettolide, amylcinnamaldehyde, anethole, anisaldehyde, anisyl alcohol, anisole, methyl anthranilate, acetophenone, benzylacetone, benzaldehyde, ethyl benzoate, benzophenone, benzyl alcohol, benzyl acetate, benzyl benzoate, benzyl formate, benzyl valerate, borneol, bornyl acetate, bromostyrene, n-decylaldehyde, n-dodecylaldehyde, eugenol, eugenol methyl ether, eucalyptol, farnesol, fenchone, fenchyl acetate, geranyl acetate, geranyl formate, heliotropin, methyl heptynecarboxylate, heptaldehyde, hydroquinone dimethyl ether, hydroxycinnamaldehyde, hydroxycinnamyl alcohol, indole, iron, isoeugenol, isoeugenol methyl ether, isosafrol, jasmone, camphor, carvacrol, carvone, p-cresol methyl ether, coumarin, p-methoxyacetophenone, methyl n-amyl ketone, methyl methylanthranilate, p-methylacetophenone, methylchavicol, p-methylquinoline, methyl β-naphthyl ketone, methyl-n-nonylacetaldehyde, methyl n-nonyl ketone, muscone, β-naphthol ethyl ether, β-naphthol methyl ether, nerol, nitrobenzene, n-nonylaldehyde, nonyl alcohol, n-octylaldehyde, p-oxyacetophenone, pentadecanolide, β-phenylethyl alcohol, phenylacetaldehyde dimethyl acetal, phenylacetic acid, pulegone, safrol, isoamyl salicylate, methyl salicylate, hexyl salicylate, cyclohexyl salicylate, santalol, skatole, terpineol, thymene, thymol, γ-undecalactone, vanillin, ethyl vanillin, veratrum aldehyde, cinnamaldehyde, cinnamyl alcohol, cinnamic acid, ethyl cinnamate, benzyl cinnamate, alkyl isothiocyanates (alkyl mustard oils), butanedione, limonene, linalool, linalyl acetate linalyl propionate, menthol, menthone, methyl-n-heptenone, phellandrene, phenylacetaldehyde, terpinyl acetate, citral and mixtures of any of the foregoing.

Depending on the application the perfume core material can be a fragrance oil selected based on boiling point or clogP values as taught in U.S. Pat. No. 6,143,707. In certain embodiments of the composition, the perfume core can be selected to have a clogP value of at least 3 and a boiling point of less than 260° C. In a yet further embodiment, the perfume core can be selected based on molecular weight, density, diffusivity and/or partition coefficient to effect either a flash fragrance or a more sustained fragrance or both as desired for the end use application. Higher molecular weights and lower vapor pressures typically are more sustained odorant effects. The advantage of the invention is that microencapsulating the perfume core material makes possible postponing the expression of even flash or volatile or fleeting fragrance oils until the cleaning solution is delivered to the situs where release is desired thus enhancing the perceived fragrant effect. The capsules of the invention deliver the fragrance oil and desirably release the fragrance upon evaporation of the water carrier of the cleaning composition.

Perfume core materials that are flash fragrances are described in US 2008/0176781 as having an acceleration value above 900 cm/sec$^2$. Examples of perfume core materials having an acceleration value greater than 900 cm/sec$^2$ include:
ethyl formate;
ethyl acetate;
ethyl propionate;
ethyl 2-methylpropanoate;
methyl hexyl ether;
2,6,6-Trimethylbicyclo-(3,1,1)-2-heptene;
butyl butyrate;
ethyl isovalerate;
ethyl butyrate;
ethyl-2-methylbutyrate;
butyl acetate;
hexanal;
isopropyl-methyl-2-butyrate;
beta.-methyl butyl acetate;
6,6-dimethyl-2-methylenenorphane;
pentyl acetate;
propyl butyrate;
7-methyl-3-methylene-1,6-octadiene;
(R)-(+)-p-Mentha-1,8-diene;
2,6-Dimethyl-2-heptanol;
2-ethenyl-2,6,6-trimethyltetrahydropyran;
E-2-hexenal;
4-isopropyl-1-methyl-1,5-cyclohexadiene;
cis-4-heptenal;
methyl phenyl ether;
1-methyl-4-isopropyl-1,4-cyclohexadiene;
ethyl 2-methylpentanoate;
3-methyl-2-butenyl acetate;
hexyl formate;
1-methyl-4-isopropylidene-1-cyclohexene;
1,3,3-trimethyl-2-oxabicyclo[2.2.2]octane;
2,3-butanedione;
3,7-dimethyl-1,3,6-octatriene;
ethyl hexanoate;
cis-3-hexenyl formate;
6-methyl-5-hepten-2-one;
3-octanone;
trans-2-hexenyl acetate;
2,2-Dimethyl-3-(3-methyl-2,4-pentadienyl)-oxirane;
2-(2'-methyl-1'-propenyl)-4-methyltetrahydropyran;
Octanal;
hexyl acetate;
methyl-2,2-dimethyl-6-methylene-1-cyclohexanecarboxylate[0105]phenylethyl methyl ether;
methyl phenyl carbinyl acetate;
3,3-dimethyl-8,9-dinorbornan-2-one;
isobutyl cis-2-methyl-2-butenoate;
cis-4-(isopropyl)-cyclohexane methanol;
isoamyl butyrate;
2,6-dimethyl-2-hepten-7-ol;
pentyl butyrate;
tricyclo decenyl acetate;
5-methyl-2-(2-methylpropyl)-cis-3-Propylbicyclo(2.2.2) hept-5-ene-2-carbaldehyde;
Methyl trans-1,4-dimethylcyclohexanecarboxylate;
1,3-Dimethylbutyl-2-butenoate;
4-(1-Methoxy-1-methylethyl)-1-methylcyclohexene;
2-Methyl-1,5-dioxaspiro[5.5]undecane;
3,6-Dihydro-4-methyl-2-(2-methylpropen-1-yl)-2H-pyran;
2-Propenyl hexanoate;
cis-3-hexenyl isobutyrate;
ethyl heptanoate;
2,4-dimethyl-3-cyclohexen-1-carbaldehyde;
cis-3-hexenyl methyl carbonate;
1-Ethyl-3-methoxytricyclo[2.2.1.02.6]heptanes;
1-(3,3-Dimethylcyclohexyl)ethan-1-one;
Nonanal;
trans-2-hexenol;
ol-1,7,7-Trimethylbicyclo[2.2.1]heptan-2-one 1,3-Dimethylbut-3-enyl isobutyrate;
cis-3-hexenol;
3,7-dimethyl-7-methoxyoctan-2-ol;
Methyl cyclopentylidene acetate;
Benzaldehyde;
Aldehyde C-6 dimethyl acetal;
3,7-Dimethyl-1,6-octadien-3-yl formate;
3,7-Dimethyloctanal;
2,6-dimethyl-2-heptanol;
4,5,6,7-Tetrahydro-3,6-dimethylbenzofuran;
1,3,5-Undecatriene;
2,5-dimethyl-2-octen-6-one;
cis-3-hexenyl acetate;
butyl 2-methyl pentanoate;
3,7-Dimethyl-6-octenal;
dimethyloctenone;

2,4-Dimethyltetrahydro benzaldehyde;
cis-3-hexenyl propionate;
2-isopropyl-5-methylcyclohexanone (isomer unspecified);
2-(1-Ethylpentyl)-1,3-dioxolane;
3-octanol;
2-phenylpropanal;
3,5,5-trimethyl hexanal;
1,3-undecadien-5-yne;
1-p-menthene-8-thiol;
1-Phenyl-4-methyl-3-oxapentane;
3,7-Dimethyl-3,6-octadienal;
3-Octenol;
E-4-Decenal;
cis-4-decenal;
phenylacetaldehyde;
2-(1-methylpropyl)cyclohexanone;
2-Butyl-4,4,6-trimethyl-1,3-dioxane;
cyclohexyl ethyl acetate;
1-octen-3-ol;
Tricyclodecenylpropionate;
6-Butyl-2,4-dimethyldihydropyrane;
2,6-nonadienal;
3-phenyl butanal;
37-dimethyl-2,6-octadiene-1-nitrile; and
Z-6-nonenal.

Materials useful as perfume core materials that are characterized as a more sustained fragrance or odorant are taught as having an acceleration value of between 900 and 100 cm/sec$^2$ inclusive include:
3-phenyl butanal;
3,7-dimethyl-6-octenol;
2,6-dimethyl-7-octen-2-ol;
6-Butyl-2,4-dimethyldihydropyrane;
3,7-Dimethyl-2,6-octadienal;
cyclohexyl ethyl acetate;
3a,4,5,6,7,7a-Hexahydro-5-methoxy-4,7-methano-1H-indene;
methyl-2-octynoate;
decanal;
3,-Dimethyl-1-octen-7-ol;
(Z)-1-(1-Methoxypropoxy)hex-3-ene;
Nonen acid nitrile;
(Z)-3,4,5,6,6-Pentamethylhept-3-en-2-one;
2-Butyl-4,4,6-trimethyl-1,3-dioxane;
2-Heptytetrahydrofuran;
hexyl butyrate;
Ethyl octanoate;
2,2,5-Trimethyl-4-hexenal dimethyl acetal;
Tricyclodecenylpropionate;
p-cresyl acetate;
2-propenyl heptanoate;
2-methyl-3-(4-methoxyphenyl)propanal;
Exo-1,7,7-trimethylbicyclo[2.2.1]hept-2-yl acetate;
benzyl acetate;
2,6-dimethyl-2-octanol;
3,7-Dimethyl-2,6-octadien-1-thiol;
Methyl 2-nonenoate;
4-Methyl-1-oxaspiro[5.5]undecan-4-ol;
2-Pentylcyclopentan-1-one;
3,7-Dimethyl-1,6-octadien-3-ol;
ethyl acetoacetate;
Decyl methyl ether;
1-Methyl-4-isopropenyl-6-cyclohexen-2-one;
n-Hexyl 2-butenoate;
3,7-Dimethyl-1,6-octadien-3-ol acetate;
p-Menth-1-en-8-yl acetate;
3,7-Dimethyloctan-3-yl acetate;
2-Methyl-4-propyl-1,3-oxalthiane;
alpha.,3,3-Trimethylcyclohexylmethyl acetate;
alpha.,3,3-Trimethylcyclohexylmethyl formate;
3-phenylpropanol;
1,3,3-Trimethylbicyclo(2.2.1)heptan-2-ol;
2-Pentyl-3-methyl-2-cyclopenten-1-one;
3,7-Dimethyl-6-octen-3-ol;
o-t-butylycyclohexyl acetate;
4-(1,1-Dimethylpropyl)cyclohexanone;
Ethylacetoacetate ethylene glycol ketal;
3-Methylene-7-methyl-1-octen-7-yl acetate;
4-methylphenylacetaldehyde;
3,5,5-trimethylhexyl acetate;
4-Methoxy-1-propenylbenzene (E);
p-Manthan-6-yl acetate;
nonyl acetate;
isolongifolene oxide;
methyl-2-nonynoate;
benzyl propionate;
4-methoxyacetophenone;
3,7-dimethyloctan-3-ol;
1,7,7-Trimethylbicyclo(2.2.1)heptan-2-ol  3,7-Dimethyl-2-methylenocta-6-enal;
phenylacetaldehyde dimethyl acetal;
1-Methyl-4-isopropyl-3-cyclohexen-1-ol;
ethyl 2,6,6-trimethyl-1,3-cyclohexadiene-1-carboxylate;
2,4-Dimethyl-4-phenyltetrahydrofuran;
Ethyl propanedioate;
2,6-dimethyl-7-octenyl-2-yl acetate;
(Z)-3,7-Dimethylocta-2,6-dienenitrile;
exo-1,7,7-Trimethylbicyclo(2.2.1)hept-2-ylpropionate;
cis-3,7-Dimethyl-2,6-octadien-1-yl ethanoate;
3-Methyl-4-(2,6,6-trimethylcyclohex-1-enyl)but-3-en-2-one;
2-Isopropanyl-5-methylhex-4-enyl acetate;
2,4-Dimethylcyclohexylmethyl acetate;
3,5-Dimethylcyclohex-3-ene-1-methyl acetate;
VERDORACINE;
1-Phenylethyl propionate;
2,4-Dimethylcyclohex-3-ene-1-methanol;
p-Isopropylbenzaldehyde;
undecanal;
2-ethylidene-6-isopropoxy-bicyclo[2.2.1]heptanes;
3-Methyl-5-propyl-2-cyclohex-1-one;
8,8-dimethyl-7-[1-methylethyl]-6,10-dioxaspiro[4,5]decane;
3,7-Dimethyl-1,6-octadien-3-yl propionate;
2-Methyldecanal;
1,1-Dimethoxy-2-phenylpropane;
c-tertiary butyl cyclohexanol;
(2E,6Z)-nona-2,6-dienenitrile;
4-n-Butyl-4-hydroxybutyric acid lactone;
CRESSANTHER;
3,7-dimethyl-6-octen-1-yl formate;
2-Phenylethyl acetate;
3,7-dimethyl-6-octenl-1-yl acetate;
8,9-epoxy cedrane;
p-isopropylcyclohexanol;
2,6-dimethyl-2-octanol;
4-Isopropyl cyclohexanol;
p-tert-Butylcyclohexyl acetate;
cis-6-nonenol;
5-Methyl-2-(1-methylethyl)cyclohexanol;
.gamma.-methylionone;
Ethyl 2,4-dimethyldioxolane-2-acetate;
1-Methyl-4-isopropylcyclohexane-8-ol;

JASMATONE™ (Perfumer's Apprentice, Santa Cruz, Calif.);
3,7-Dimethyl-1-octen-7-ol;
cis-3-hexenyl methylbutyrate;
phenylethyl formate;
trans-3,7-Dimethyl-2,6-octadien-1-yl acetate;
4-(2,6,6-Trimethyl-1-cyclohexen-1-yl)-3-buten-2-one;
2,4-dimethyl cyclohexane methanol;
cis-6-Methyl-1-oxaspiro[4.5]decan-2-one;
2-Methylpent-2-en-1-oic acid;
1.a.,3.a.,6.a.)-2',2',3,7,7-Pentamethylspiro(bicyclo[4.1.0] heptane-2,5'-(1.3)dioxane;
g-nonalactone;
10-undecenal;
alpha.-ionone; 1-methyl-1-methoxycyclododecane;
3,7-Dimethyl-1,6-octadien-3-yl 2-methylpropanoate;
2,2,5-trimethyl-5-pentylcyclopentanone;
cumin nitrile;
4-Methoxybenzyl acetate;
3,7-Dimethyl-1,6-nonadien-3-ol;
cis-2,6-Dimethyl-2,6-octadien-8-ol;
spiro[furan-2(3H), 5'-(4,-methane-5H-indene)], decahydro ethyl safranate;
1-p-Menthen-8-ol, 1-Methyl-4-isopropyl-1-cyclohexen-8-ol
5,9-Dimethyl-4,8-decadienal benzyl-n-butyrate;
(E)-3,7-Dimethyl-2,6-octadienyl 2-methylcrotonate;
2-Methyl-3-phenyl-2-propenal;
o-t-amyl-cyclohexanyl acetate;
3,6-dihydro-4-methyl-2-phenyl-2H-pyran;
Octyl 2-methylpropanoate;
dimethyl benzyl carbinyl acetate;
3-Methyl-1,4-octalactone;
2-Methyl-4-phenyl-2-butanol;
2,6-Nonadienol;
Isobutyl phenylacetate;
(R-(E))-1-(2,6,6-Trimethyl-2-cyclohexen-1-yl)pent-1-en-3-one[0463]LEVISTAMEL;
3,7-dimethyl-1,6-nonadien-3-yl acetate;
1-(2,4-Dimethyl-3-cyclohexenyl)-2,2-dimethylpropan-1-one[0466].alpha.,.alpha.-dimethylphenethyl alcohol;
(E)-1-(2,4,4-Trimethyl-2-cyclohexen-1-yl)-2-buten-1-one;
1-(2,6,6-Trimethyl-1-cyclohexen-1-yl)pent-1-en-3-one;
2,4,6-Trimethyl-3-cyclohexene-1-methanol;
trans-3,7-Dimethyl-2,7-octadien-1-ol;
1,1-Diethoxy-3,7-dimethyl-2,6-octadiene;
1-Phenyl-4-penten-1-one;
cedryl methyl ether;
1-Methyl-4-isoproenylcyclohexan-3-ol;
phenylethyl isoamyl ether;
3-Methylene-7-methyl-1-octene-7-yl acetate;
6-ethylideneoctahydro-5,8-methano-2H-benzopyran;
3,7-Dimethyl-1-octanol;
3,7-Dimethyl-1,6-octadien-3-yl butyrate;
2-hexyl-2-cyclopenten-1-one;
Methoxycyclodecan;
1-Cyclohexylethyl 2-butenoate;
5,6-epoxy-2,6,10,10-tetramethylbicyclo[7.2.0]undecane;
Tetrahydro-4-methyl-2-phenyl-2H-pyran;
acetaldehyde ethyl phenylethyl acetal;
trans-3,7-Dimethyl-2,6-octadien-1-yl propionate;
6,10-dimethyl-5,9-undecadien-2-one;
6-Methyl-2-(4-methylcyclohex-3-enyl)hept-1,5-diene;
3-Methyl-2-(2-pentenyl)-2-cyclopenten-1-one isomers;
2-ethoxy-9-methylen-2,6,6-trimethylbicyclo[3.3.1]nonane
[0491]Tetrahydro-4-methyl-2-propyl-2H-pyran-4-yl acetate;
trans-3,7-Dimethyl-2,6-octadien-1-yl isobutyrate;

p-Methyltetrahydroquinone;
decahydro-b-naphtyl acetate;
dodecanal;
1-phenylethyl alcohol;
(E)-7,11-Dimethyl-3-methylenedodeca-1,6,10-triene;
3-(isopropylphenyl)butanal;
ethyl-2-ethyl-6,6-dimethyl-2-cyclohexane;
3,7-dimethyl-2(3),6-nonadienenitrile;
6-methyl-.beta.-ionone;
7-methoxy-3,-dimethyloctanal;
(Z)-1-(2,6,6-Trimethyl-1-cyclohexen-1-yl)-2-buten-1-one;
Allyl(3-methylbutoxy)acetate;
4-(2,5,6,6-Tetramethyl-2-cyclohexen-1-yl)-3-buten-2-one;
3-Methyl-2-butenyl benzoate;
3-(4-ethylphenyl)-2,2-dimethylpropanal;
3,5,6,6-tetramethyl-4-methyleneheptan-2-ol;
5-1-(2,6,6-Trimethyl-3-cyclohexen-1-yl)-2-buten-1-one;
ethyl tricyclo[5.2.1.02.6]decan-2-carboxylate;
.alpha.-1-(2.6,6-Trimethyl-2-cyclohexen-1-yl)-2-buten-1-one;
9-decanol;
undecene 2 nitrile;
Ethyl 2-nonynoate;
3,4,4a,5,8,8a-Hexahydro-3',7-dimethylspiro[1,4-methanon-aphthalene-2-(1H),Z-oxirane];
p-tert-butylphenylacetonitrile;
Ethyl 2,3-epoxy-3-methyl-3-phenylpropionate;
3,6-Dihydro-2,4-dimethyl-6-phenyl-2H-pyran;
cis-trans-2-Methyl-2-vinyl-5(2-hydroxy-2-propyl)tetrahydrofuran;
4-methyl-3-decene-5-ol;
Octahydro-4,7-methano-1H-indene-5-yl acetate;
2-Methylundecanal;
2-heptyl cyclopentanone;
Ethyl(2R/S,3R/S)-3-isopropylbicyclo[2.2.1]hept-5-ene-2-carboxylate;
6-sec-Butylquinoline;
alkyl cyclohexyloxyacetate;
5-phenyl-5-methyl-3-hexanone;
DISPIRONE™ (Quest International, Naarden, NL);
3-(4-tert-butylphenyl)propanal;
3,7-Dimethyl-6-octen-1-yl propanoate;
phenylethyl isobutyrate;
1,2,3,4,5,6,7,8-Octahydro-8,8-dimethyl-2-naphthaldehyde;
1-(5,5-Dimethyl-1-cyclohexen-1-yl)pent-4-en-1-one;
Methyl 2-hydroxybenzoate;
Ethyl linalyl acetal;
allyl cyclohexyl propionate;
3,7-Dimethyl-6-octen-1-yl 2-methylpropanoate;
INDOCLEAR;
AZARBRE;
2-Phenoxyethyl propionate;
Ethyl 2-methoxybenzoate;
3-Phenyl-2-propenal;
2,2-Dimethyl-3-(p-ethylphenyl)propanal;
2,7-Dimethyl-10-(1-methylethyl)-1-oxaspiro[4.5]deca-3,6-diene[0545]1,3,4,6,7,8a-Hexahydro-1,1,5,5-tetramethyl-2H-2,4a-methanonaphthale-n-8(5H)-one;
5-methyl-3-heptanone oxime;
cis-3-hexenyl benzoate;
2,3,4,5,6,7,8-Octahydro-8,8-dimethyl-2-naphthaldehyde;
5-Hydroxyundecanoic acid lactone;
4-methoxybenzaldehyde;
4-methyl-3-decen-5-ol;
4-n-Hexyl-4-hydroxybutanoic acid lactone;
Allyl(2-methylbutoxy)acetate;
p-Mentha-8-thiol-3-one;

dodecahydro-3a,6,6,9a-tetramethylnaphto(2,1-b)-furan;
5-methyl-3-heptanone oxime;
4-(1-ethoxyvinyl)-3,5,5,5-tetramethylcyclo-hexanone;
2-(4-tert-butylbenzyl)propionaldehyde;
Cyclohexyl lactone;
Decanol;
1-(2,6,6-Trimethylcyclohexa-1,3-dienyl)-2-buten-1-one;
2-methyl-3-(4-isopropylphenyl)propanal; and
1-(4-isopropylcyclohexyl)-ethanol.

Materials useful as perfume core materials that are characterized as delayed release fragrances or odorants are taught as having an acceleration value of less than 100 cm/sec$^2$. These materials characterized as deposition materials, are desirable because of ability to result in substantial deposition onto a surface. The capsule system of the invention makes possible more sustained delivery of fragrance by postponing a substantial portion of the fragrance expression until capsule delivery and capsule wall disintegration upon carrier drying leading to fragrance release from perfume core material deposition onto the surface.

Materials useful as perfume core materials characterized as having an acceleration value of less than 100 cm/sec$^2$ include:
2-Isobutyl-4-methyltetrahydro-2H-pyran-4-ol;
.alpha.-Amino methylbenzoate;
1-(2,6,6-Trimethyl-2-cyclohexene-1-yl)-1,6-heptadien-3-one;
3,7-Dimethyl-6-octenyl 3-methylbutanoate;
4-Methoxybenzaldehyde diethyl acetal;
[2-(Cyclohexyloxy)ethyl]benzene;
AGARBOIS™ (Quest International, Naarden, NL);
2-Methoxy-4-(2-propenyl)phenol;
2(6)-methyl-8-(1-methylethyl)bicyclo[2.2.2]octa-5-en-2(3)-yl-1,3-di-oxolane[0179]2-Methyl-4-(2,2,3-trimethyl-3-cyclopenten-1-yl)-2-buten-1-ol;
3-Phenylpropyl alcohol;
2-(Phenylmethylene)heptanal;
Ethyl(2E,4Z)-decadienoate;
7-Methyl-2H-benzo-1,5-dioxepin-3(4H)-one;
Ethyl 2-hexylacetoacetate;
4,4a,5,9b-Tetrahydroindeno[1,2-d]-1,3-dioxine;
3-Methyl-5-phenylpentanenitrile;
3,4-Dihydro-2H-1-benzopyran-2-one;
2-Phenoxyethyl isobutyrate-Dodecanenitrile;
2-(3-Phenylpropyl)pyridine;
2,6,19-trimethyl-5,9-undecadienal;
p-Isobutyl-a-methyl hydrocinnemaldehyde;
trans-3,7-Dimethyl-2,6-octadien-1-yl-3-methylbutanoate;
6-.beta.-H-Cedran-8-ol, acetate;
VETHYMINE™ (2,4-diethoxy-5-methylpyrimidine);
Tricyclo(5.2.1.02.6)dec-3-en-9-ylisobutyrate;
Trimethyl-13-oxabicyclo[10.1.0]trideca-4,8-diene;
3,7-Dimethyl-7-hydroxyoctanal;
2-Benzyl-4,4,6-trimethyl-1,3-dioxane;
amberketal;
2,6,10-Trimethyl-9-undecenal;
.gamma.-undecalactone;
10-undecen-1-ol;
1,2-Benzopyrone;
4-(p-Methoxyphenyl)-2-butanone;
3-Butyltetrahydro-5-methyl-2H-pyran-4-ylacetate;
3(Or 4)-(4-methylpenten-3-yl)cyclohex-3-ene-1-methyl acetate;
6,10-dimethyl-9-undecen-2-one;
carbonic acid:4-cyclootene-1-yl:methyl ester;
2-(2-Methylphenyl)ethanol;
a,a-Dimethylphenethyl butyrate;
4-Hydroxy-3-methoxy-1-propenylbenzene;
1,5,5,9-Tetramethyl-13-oxatricyclo(8.3.0.0(4,9)tridecane);
2-Methyl-4-(2,2,3-trimethyl-3-cyclopentenyl)butanol;
2-isobutoxynaphthalene;
3,7,11-Trimethyl-2,6,10-dodecatrien-1-ol;
Methoxy dicyclopentadiene carboxyaldehyde;
1,1'-Bicyclopentyl-2-yl 2-butenoate; 2-Cyclopentylcyclopentyl crotonate; [0219]methyl-2-naphtyl ketone;
1,2,3,4,4a,5,6,7-Octahydro-2,5,5-trimethyl-2-naphthol;
2H-Pyran-2-one, tetrahydro-6-(3-pentenyl);
3-methyldodecanonitrile;
Dihydro-5-octylfuran-2(3H)-one;
1,2,3,4,4a,7,8,8a-Octahydro-2,4a,5,8a-tetramethyl-1-naphthyl formate FRUTONILE;
magnolian;
3-Methyl-5-phenylpentanol;
(E) and (Z) 6,10-Dimethylundeca-5,9-dien-2-yl acetate;
alcohol C-12, dodecanol;
5,6-Dimethyl-8-isopropenylbicyclo(4.4.0)dec-1-en-3-one;
2-methyl-5-phenylpentanol;
3-methyl-5-phenylpentanol;
2-Methoxy-4-propenylphenyl acetate;
1-(1,2,3,4,5,6,7,8-Octahydro-2,3,8,8-tetramethyl-2-naphthaleneyl)et-hanone;
Tricyclo[6.3.1.02.5]dodecan-1-ol,4,4,8-trimethyl-,acetate, [1R-(1a,2a,5b,8b)]-;
PIVACYLENE;
Ethyl a,b-epoxy-b-phenylpropionate;
3-(4-ethyl phenyl)-2,2-dimethylproapanenitrile;
(1R-(1a,4b,4ae,6b,8ae))-Octahydro-4,8a,9,9-tetramethyl-1,6-methano-1(2H)-naphthol;
2-methyl-3-(3,4-methylenedioxyphenyl)propanol;
3-Methylbutyl alpha.-hydroxybenzoate;
2-Ethyl-4-(2,2,3-trimethyl-3-cyclopenten-1-yl)-2-buten-1-ol;
1,3-Benzodioxole-5-carboxaldehyde;
benzyl alcohol;
1-Phenyl-3-methyl-3-pentanol;
2-Ethyl-2-prenyl-3-hexenol;
4-Acetyl-6-t-butyl-1,1-dimethylindan;
.alpha.-hexylcinnamic aldehyde;
2-Oxo-1,2-benzopyran;
3aR-(3aa,5ab,9aa,9bb)Dodecahydro-3a,6,6,9a-tetramethylnaphtho(2,1-b-)furan;
hydroxycitronella)dimethyl acetal;
2-Methyl-4-phenylpentanol;
3,7,11-Trimethyldodeca-1,6,10-trien-3-ol mixed isomers;
a,b,2,2,3-Pentamethylcyclopent-3-ene-1-butanol;
3,12-tridecadien-nitrile;
3a,4,5,6,7,7a-Hexahydro-2,6(or 3,6)dimethyl-4,7-methane-1H-inden-5-ol[0257]3-Phenyl-2-propan-1-ol;
4-(2,6,6-Trimethylcyclohexyl)-3methylbutan-2-ol;
4-(3,4-Methylenedioxyphenyl)-2-butanone;
3,4-dimethoxybenzaldehyde;
SINODOR™ (Quest International, Naarden, NL);
3-Methyl-5-(2,2,3-trimethyl-3-cyclopenten-1-yl)pent-4-en-2-ol;
Ethoxymethoxy)cyclodecane;
2-ethoxy-4-methoxymethylphenol;
2-[2-(4-Methylcyclohex-3-en-1-yl)propyl]cyclopentanone;
4-(4,8-Dimethylnona-3,7-dienyl)pyridine;
(E,E,E)-2,6,10-Trimethyldodeca-2,6,9,11-tetraen-1-al;
4-tricyclodecylidene butanal;
Methyl 3-phenylpropenoate;
7-Methyl-2H-benzo-1,5-dioxepin-3(4H)-one;
amber core;
3-(2-bornyloxy)-2-methyl-1-propanol(exo);
3-Phenyl-2-propen-1-yl 3-methylbutanoate;

trans-2,4-Dimethyl-2-(5,6,7,8-tetrahydro-5,5,8,8-tetramethyl-2-naph-thalenyl)-1,3-dioxolan;
a-Cyclohexylidene benzeneacetonitrile;
3-(Hydroxymethyl)nonan-2-one;
Benzoic acid, 2-hydroxy-, 3-methyl-2-butenyl ester;
cedryl methyl ketone;
cis-4-Cyclopentadecenone;
6-Ethyldineoctahydro-5,8-methano-2H-1-benzopyran-2-one;
6-cyclohexadecen-1-one;
cyclopentadecanone;
3,3-Dimethyl-5-(2,2,3-trimethyl-3-cyclopenten-1-yl)-4-penten-2-ol[0285]methyl dihydrojasmonate;
Cyclopentadecanolide;
1,3-Dioxane,2-(2,4-dimethyl-3-cyclohexene-1-yl)-5-methyl-5-(1-methylpropyl)-3,7-dimethyl-1,6-octadien-3-yl benzoate;
Methyl(2-pent-2-enyl-3-oxo-1-cyclopentyl)acetate;
2-tert-butylcyclohexyl carbonate;
4-(4-hydroxyphenyl)-2-butanone;
1,3,4,6,7,8-Hexahydro-4,6,6,7,8,8-hexamethylcyclopenta-.gamma.-2-benzopyran;
methyl-2-hexyl-3-oxocyclopentanedecarboxylate; and
3-methylcyclopentadecanone.

Typically the majority of the capsules formed by coacervation in the present invention range in size from about 10 nanometers to about 1000 microns, preferably from about 50 nanometers to about 100 microns, and most preferably from about 10 to 50 microns. These capsules typically are of a fairly wide size distribution with substantial quantities of diverse capsule sizes occurring across the range. The particular particle size and/or particle size distribution is not critical to practice of the present invention.

As used herein, "core material" or "core component" is intended to mean all the material encapsulated by the microcapsule wall material forming the internal content of the microcapsule. The fragrance core material used in the present invention is typically fluid and can include solvent and other dissolved components.

The core material is present in the microcapsule from about 0.1%, from about 1% or even from about 5% by weight based on the total weight of the microcapsule to about 30%, to about 55%, to about 80% or even to about 99%. Preferably, the core material is present in the microcapsule at a level of from about 1 to 99% by weight based on the total weight of the microcapsule, which includes the weight of the encompassing shell material. Typically, the core material is present in an amount of from about 30 to about 90% by weight, based on the total weight of the microcapsule. The respective amount of core material present is not critical to practice of the present invention.

The fragrance-containing microcapsules of the present invention can be made by conventional coacervation procedures. A polyvinyl alcohol aqueous solution is provided comprising from about 3 to about 25% solids of polyvinyl alcohol. The polyvinyl alcohol is combined with water in a reactor together with the emulsifiable fragrance component (typically in the form of an oil). High shear is applied by means, for example, of a suitable stirring means until the desired emulsion is obtained having the desired particle sizes. The shear and type required can vary as long as the outcome or particle size distribution is achieved. The distribution can be very broad or very narrow depending on the type of performance desired from the end user. Once the desired emulsion is obtained, a source of boron ions such as a 1% solution of Borax salt (sodium tetraborate) is added incrementally (such as drop-wise) under light stirring to obtain boron ion-crosslinked polyvinyl alcohol microcapsules containing a fragrant core material. The particle size of the capsules can range from 2 microns to 150 microns. The distributions can be bimodal, trimodal or have a very narrow distribution. The most desired outcome of milling is 20 microns with bimodal distribution. The above process occurs at ambient temperature in the absence of added heat input.

Upon the addition of the Borax salt, for instance, or persulfate salt, the salt dissolves to form boric acid which, in its hydrolyzed form, serves as a crosslinking agent with respective molecules of polyvinyl alcohol via a condensation reaction. While in the presence of water, the crosslinked polyvinyl alcohol microcapsules retain their flexibility, but return to a solid phase upon being dried, resulting in the disintegration of the microcapsule and the release of the core fragrance material.

Persulfate salt similarly was found to serve as a similar cross-linking agent with respect to polyvinylalcohol.

Capsules formed using persulfate salts similarly retained flexibility in the presence of water but returned to a solid phase and upon being dried the capsules disintegrated releasing the core contents, resulting in deposition of the core agricultural materials on the site of application.

The microcapsules of the present invention have multiple end uses. For instance, such microcapsules find particular utility in the application of a fragrance to a substrate in order to, for instance, counteract malodors. In such an embodiment, the microcapsules are applied in the form of an aqueous suspension of the microcapsules by any convenient manner, such as by spraying (preferably without the use of propellants), the use of trigger sprayers, aerosols, pump sprayers, mops, absorbent wipes, etc. The composition is preferably applied directly to a hard surface (as opposed to spraying in the air and being permitted to fall or disperse onto the hard surface) such as a floor, kitchen countertop, bathroom countertop, etc. Once applied, as the aqueous suspension dries, the microcapsules will also dry (causing the polyvinyl alcohol to revert to solid form), whereby the fragrant core material is caused to be released.

In an alternate embodiment, the composition may serve as a cleaning composition as well as a malodor-treating composition, such that a cleaning component is present in addition to the fragrance-containing microcapsules. In such an embodiment, the composition would also be wiped on the hard surface to facilitate cleaning of the surface, during which the fragrance core material is released onto the hard surface.

The composition of the present invention finds utility in a variety of environments, such as but not being limited to areas of heavy pedestrian usage, such as airports, railroad stations, offices, hospitals, shopping malls, public buildings, theatres, cinemas, auditoriums, washrooms, hotels, health clubs, night clubs, restaurants, bars, gyms, sports arenas, public transportation (trains, planes, etc.), as well as homes and private vehicles. Additional utility may be found with respect to soft furnishings, upholstery, curtains, car seats, carpets, bedspreads, clothes, shoes, etc. Indeed, the types of surfaces to which the composition of the present invention may be applied in order to be able to achieve the benefits of the invention are essentially endless.

The compositions of the present invention may be formed by any suitable method. For instance, an aqueous dispersion of the microcapsules of the present invention may be combined with suitable adjuvants such as cleaning components. The microcapsules are not dried prior to forming the composition, as such drying would cause the microcapsules to prematurely disintegrate.

As noted previously, the microcapsules of the present invention find utility in cleaning compositions such as for hard surfaces. Such compositions typically are comprised of one or more of surfactants, hydrophilic polymers, organic cleaning solvents, mono- or polycarboxylic acids, odor control agents, a source of peroxide, a thickening polymer, a suds suppressor, a perfume, antimicrobial agents, and a detergent adjuvant. Such a cleaner would generally be comprised of an aqueous solvent system.

Cleaning compositions are well known to those skilled in the art, as evidenced by the disclosures of U.S. Pat. Nos. 6,936,580; 7,082,951; 7,163,349; and 7,199,094, the disclosures of which are herein incorporated by reference.

Suitable surfactants typically are comprised of alkylpolysaccharides, alkyl ethoxylates, alkyl sulfonates, and mixtures thereof, and are generally present in an amount of from about 0.001 to about 0.5% by weight. Hydrophilic polymers may be used to increase the hydrophilicity of the surface to be treated. A variety of hydrophilic polymers may be used, including but not limited to those containing hydrophilic groups such as amine oxide, sulfonate, pyrrolidone, and carboxylate groups, and are generally present in an amount of up to 0.5% by weight. Such polymers generally have a molecular weight of from 10,000 to 1,000,000. Typical organic cleaning solvents are generally present in an amount of from about 0.5 to 7% by weight, and may include such solvents as monopropylene glycol mono-propyl ether, di-propylene glycol mono-propyl ether, mono-propylene glycol mono-butyl ether, di-propylene glycol mono-propyl ether, di-propylene glycol mono-butyl ether; tri-propylene glycol mono-butyl ether; ethylene glycol mono-butyl ether; di-ethylene glycol mono-butyl ether, ethylene glycol mono-hexyl ether and di-ethylene glycol mono-hexyl ether, 3-methoxy-3-methyl-butanol, and mixtures thereof. The presence of the organic solvent serves to assist the surfactant in removal of dirt from the hard surface. Mono- and polycarboxylic acids may be used to assist in the removal of soap scum and hard water stains from a hard surface, and may include acetic acid, glycolic acid or beta.-hydroxy propionic acid, citric acid, tartaric acid, succinic acid, glutaric acid, adipic acid, and mixtures thereof. Peroxides such as benzoyl peroxide and hydrogen peroxide may be present in an amount of from about 0.05 to about 5% by weight. A thickening polymer such as xanthan gum can be employed with advantage in an amount of from about 0.001 to about 0.1% by weight. The cleaning composition will further typically be comprised of an aqueous solvent system, which comprises from about 80 to about 99% by weight of the composition. Water-soluble organic solvent components may also be present in minor amounts, such as lower alcohols including but not limited to methanol, ethanol, isopropanol, n-butanol, iso-butanol, 2-butanol, pentanol, methoxymethanol, methoxyethanol, methoxy propanol, and mixtures thereof.

The identity and/or relative amounts of the above components can be readily determined by one skilled in the art, taking into account factors such as the type of cleaning to be undertaken, the manner by which the composition is to be applied, the identity of the substrate to be cleaned, etc. Indeed, the present invention has applicability in household, institutional and industrial uses.

The microcapsules of the present invention also find utility in a variety of types of additional compositions which may normally contain a fragrance component, such as personal care and fabric care products. Such compositions include but are not limited to rinse-off or wash-off products such as laundry detergents, fabric softeners, dish detergents, and pet shampoos, as well as a variety of personal care products (rinse-off or not) such as hair shampoos, hair conditioners, hair rinses, body creams and washes, hair colors and dyes, etc. Such products may be in various forms, such as water-containing liquid or water-containing semi-liquid (such as gels or pastes). The composition of the present invention may accordingly include agents such as fabric softening ingredients, skin moisturizers, sun screen, insect repellant, etc.

For the purposes of the present invention, wash-off or rinse-off products include those products that are applied for a given period of time, and then are removed. Such products are commonly used as laundry products (detergents, fabric conditioners) as well as personal care products (shampoos, conditioners, hair colors, hair dyes, hair rinses, body washes, soaps, etc.).

Such materials employ a variety of components which are well known to those skilled in the art, as confirmed by the following patents, each of which is herein incorporated by reference.

The various rinse-off or wash-off products with which the microcapsules of the present invention may be employed include surfactant and emulsifying systems which are well known to those skilled in the art.

Fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, and 4,767,547, 4,424,134. Liquid dish detergents are described in U.S. Pat. Nos. 6,069,122 and 5,990,065; automatic dish detergent products are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562. Liquid laundry detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431,5,194,639, 4,968,451, 4,597,898, 4,561,998, 4,550,862, 4,537,707, 4,537,706, 4,515,705, 4,446,042, and 4,318,818. Shampoo and conditioners that can employ the present invention include those described in U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090 and 4,705,681.

The microcapsules of the present invention are further described in the following example which is intended to be merely exemplary and not limiting.

EXAMPLE 1

Boron-ion crosslinked polyvinyl alcohol microcapsules of the present invention were produced as follows. A 1% Borax solution was prepared by adding 198 grams of deionized water to a beaker while stirring with a stir bar at room temperature. 2 grams of 20 Mule Team Borax Tech 4/200 Mesh (Sodium Tetraborate Decahydrate) is added while stirring. The 1% Borax solution was allowed to mix for 10 minutes or until the material dissolved and the water was clear. A 15% polyvinyl alcohol solution was prepared by adding 595 grams of deionized water to a water jacketed vessel set to 80° C. The water was stirred with a paddle mixer while 105 grams of granular Celvol 523 is added slowly over one minute. The polyvinyl alcohol was allowed to mix and cook at this temperature for 30 minutes before being removed and cooled.

53.56 grams of 15% 523 polyvinyl alcohol were added to a 1 kg reactor to which was previously added 242.98 grams distilled water. The mixture was stirred with a 2 inch diameter, 4 point star blade mixer for a period of 5 minutes at 425 RPM. 250.63 grams of Old English Lemon Oil obtained from Rickitt Benckiser Inc. (Parsippany N.J. 07054-0224) were added while stirring. The mixture was milled with the same flat 4 point star blade, 2 inches in diameter at 3000 rpm for a period of 3 minutes to achieve microspheres having a particle size with mean at 24.01 microns, standard deviation of 10.25 microns and median of 22.98 microns.

After milling, the star mixer was changed to a paddle mixer and the slurry was allowed to mix at 700 RPM while, 8.67 grams of the 1% Borax solution was added drop-wise over a period of 5 minutes and allowed to finish mixing for another 15 minutes at 700 RPM. Approximately 1.5 parts by weight of the 1% Borax solution was added to the mixture. The boron-ion crosslinked polyvinyl alcohol microcapsules were now formed with particle size mean of 23.63 microns, standard deviation 11.67 microns and median of 22.60 microns. The final viscosity was 518 Centipoise at pH 6.4 and 45.6% solids.

The total time for the preparation of the Celvol 503 and 20 Mule Team Borax solutions was approximately 40 minutes. The microencapsulation procedure occurred at room temperature and took 22 minutes.

The capsules were collected onto a paper sheet, and the effect studied. It was observed that the paper became oil-saturated over a period of one hour, which confirmed that the microcapsules were caused to disintegrate upon being dried and exposure room temperature.

The polyvinyl alcohol was prepared from >92% by wt. acetic acid ethenyl ester polymer with ethanol, <5% by wt. water, <3% by wt. sodium acetate anhydrous, and <1% by wt. methyl alcohol.

EXAMPLE 2

54.18 grams of 15% 523 polyvinyl alcohol were added to a 1 kg reactor to which was previously added 243.00 grams distilled water. The mixture was stirred with a 2 inch diameter, 4 point star blade mixer for a period of 5 minutes at 425 RPM. 250.00 grams of Peppermint Essential Oil obtained from Aromaland Inc. (1326 Rufina Circle Santa FE, N. Mex. 87507) were added while stirring. The mixture was milled with the same flat 4 point star blade, 2 inches in diameter at 3000 rpm for a period of 3 minutes to achieve microspheres having a particle size with mean at 19.17 microns, standard deviation of 9.50 microns and median of 18.42 microns.

The star mixer was changed to a paddle mixer while 45.45 grams of the 1% Borax solution was added dropwise over 6 minutes at 700 RPM. The microcapsules were allowed to mix under these conditions for a period of 15 minutes at 700 RPM after Borax addition. Approximately 7.6 parts by weight of the 1% Borax solution was added to the mixture. The final viscosity was 328 Centipoise at pH 6.7 and 44.31% solids. The final particle size had a mean of 18.27 microns with standard deviation of 8.28 microns and median of 17.86 microns.

The capsules were placed on a sheet of paper and the paper became oil-saturated again after approximately one hour.

EXAMPLE 3

53.89 grams of 15% 523 polyvinyl alcohol were added to a 1 kg reactor to which was previously added 243.09 grams distilled water. The mixture was stirred with a 2 inch diameter, 4 point star blade mixer for a period of 5 minutes at 425 RPM. 249.82 grams of Cedarwood Essential Oil obtained from Aromaland Inc. (1326 Rufina Circle Santa FE, N. Mex. 87507) were added while stirring. The mixture was milled with the same flat 4 point star blade, 2 inches in diameter at 3000 rpm for a period of 5 minutes to achieve microspheres having a particle size with mean at 23.69 microns, standard deviation of 12.63 microns and median of 23.38 microns.

The star mixer was changed to a paddle mixer while 31.30 grams of the 1% Borax solution was added dropwise over 3 minutes at 700 RPM. The microcapsules were allowed to mix under these conditions for a period of 15 minutes at 700 RPM after Borax addition. Approximately 5.4 parts by weight of the 1% Borax solution was added to the mixture. The final viscosity was 679 Centipoise at pH 6.92 and 45.11% solids. The final particle size had a mean of 18.27 microns with standard deviation of 8.28 microns and median of 17.86 microns.

EXAMPLE 4

54.24 grams of 15% 523 polyvinyl alcohol were added to a 1 kg reactor to which was previously added 243.14 grams distilled water. The mixture was stirred with a 2 inch diameter, 4 point star blade mixer for a period of 5 minutes at 425 RPM. 250.91 grams of Vanilla Pound Cake oil obtained from Hosley Intl. Inc. (Lynwood Ill. 60411) were added while stirring. The mixture was milled with the same flat 4 point star blade, 2 inches in diameter at 2000 rpm for a period of 2 minutes to achieve microspheres having a particle size with mean at 10.92 microns, standard deviation of 5.28 microns and median of 9.07 microns.

The star mixer was changed to a paddle mixer while 75.84 grams of the 1% Borax solution was added dropwise over 12 minutes at 700 RPM. The microcapsules were allowed to mix under these conditions for a period of 15 minutes at 700 RPM after Borax addition. Approximately 12.15 parts by weight of the 1% Borax solution was added to the mixture. The final viscosity was 279 Centipoise at pH 7.38 and 43.89% solids. The final particle size had a mean of 10.82 microns with standard deviation of 6.65 microns and median of 8.14 microns.

EXAMPLE 5

53.89 grams of 15% 523 polyvinyl alcohol were added to a 1 kg 45° C. reactor to which was previously added 242.97 grams distilled water. The mixture was stirred with a 2 inch diameter, 4 point star blade mixer for a period of 5 minutes at 425 RPM. 250.41 grams of Lavender Oil from Hosley Intl. Inc. (Lynwood Ill. 60411) were added while stirring. The mixture was milled at 45° C. with the same flat 4 point star blade, 2 inches in diameter at 2000 rpm for a period of 3 minutes to achieve microspheres having a particle size with mean at 9.58 microns, standard deviation of 3.82 microns and median of 8.00 microns.

The star mixer was changed to a paddle mixer while 27.92 grams of the 1% Borax solution was added dropwise over 4 minutes at 300 RPM. The microcapsules were allowed to mix under these conditions for a period of 15 minutes at 300 RPM after Borax addition. Approximately 4.8 parts by weight of the 1% Borax solution was added to the mixture. The final viscosity was 375 Centipoise at pH 7.35 and 45.03% solids. The final particle size had a mean of 8.84 microns with standard deviation of 3.49 microns and median of 7.78 microns.

EXAMPLE 6

This example was made with diluent blended with a fragrance component. 54.2 grams of 15% 523 polyvinyl alcohol were added to a 1 kg reactor to which was previously added 243.01 grams distilled water. The mixture was stirred with a 2 inch diameter, 4 point star blade mixer for a period of 5 minutes at 425 RPM. 125.76 grams of Peppermint Essential Oil obtained from Aromaland Inc. (1326 Rufina Circle, Santa FE, N. Mex. 87507) and 125.12 grams of Norpar 12 obtained from Exxon (13501 Katy Freeway, Houston, Tex. 77079-1398) were mixed together for a period of 5 minutes before being added to the reactor with polyvinyl alcohol and water. The mixture was milled with the same flat 4 point star blade, 2 inches in diameter at 2500 rpm for a period of 2 minutes to achieve microspheres having a particle size with mean at 16.21 microns, standard deviation of 7.23 microns and median of 15.43 microns.

The star mixer was changed to a paddle mixer while 27.96 grams of the 1% Borax solution was added dropwise over 3 minutes at 700 RPM. The microcapsules were allowed to mix under these conditions for a period of 15 minutes at 700 RPM after Borax addition. Approximately 4.8 parts by weight of the 1% Borax solution was added to the mixture. The final viscosity was 656 Centipoise at pH 6.82 and 45.10% solids. The final particle size had a mean of 14.84 microns with standard deviation of 7.84 microns and median of 13.24 microns.

EXAMPLE 7

50 grams of 15% 523 polyvinyl alcohol are added to a heated (85° C.) 1 kg reactor to which was previously added 240 grams distilled water. The mixture is stirred with a 2 inch diameter, 4 point star blade mixer for a period of 5 minutes at 425 RPM. 25 grams of orange oil (d-limone) (Citrus Depot, St. Petersburg, Fla.) is dissolved in 225 grams of Oleocal 112 from Lambent Technologies Corp. (Methyl Ester of Canola oil, cas 67762-38-3) at 85° C. for 15 minutes with stirring. The mixture is milled at 85° C. with a flat 4 point star blade, 2 inches in diameter at 2000 rpm for a period of 3 minutes to achieve microspheres having a particle size predicted to have a mean at 28 microns, standard deviation of about 10 microns and median of about 26 microns.

After milling, the star mixer is changed to a paddle mixer and the slurry is allowed to mix at 700 RPM while 4.0 grams of Potassium Persulfate (cas 7727-21-1) from Malinckrodt Baker Inc. Phillipsburg, N.J. 08865 are added to the vessel over 30 seconds. The mixture is allowed to mix at 85° C. for 40 minutes before the heat is removed. The persulfate-ion crosslinked polyvinyl alcohol microcapsules are formed with expected particle size mean of 26 microns, standard deviation of about 12.0 microns and median of about 24 microns. The entire process is carried out at 85° C. pH of the solution is kept on the acidic side pH<>.

The above description is intended to be merely illustrative of the present invention, and not intended to be limiting thereof. Minor changes and deviations may be made herein without departing from the scope of the invention.

What is claimed is:

1. A water-containing composition comprising a suspension of microcapsules in water, the composition having a pH of from about 5.7 to about 12.8 and comprising a water phase and ion-crosslinked polyvinyl alcohol microcapsules stable in water and encapsulating a non-solvent for the water phase, wherein the ion for cross-linking is selected from the group consisting of boron and persulfate ions.

2. The composition of claim 1 comprising a fabric care, personal care, or cleaning product.

3. The composition of claim 2 comprising a fabric care product selected from a fabric detergent and fabric softener.

4. The composition of claim 2 comprising a cleaning composition.

5. The composition of claim 4 comprising a hard surface cleaner or dish detergent.

6. The composition of claim 2 comprising a personal care product selected from hair shampoo, hair conditioner, rinse, body wash, hair colorings, hair dyes, and creams.

7. The composition of claim 1, wherein said microcapsules contain at least one fragrance component as a core material.

8. The composition of claim 7, wherein said at least one fragrance component is selected from the group consisting of essential oils, flash fragrances, sustained release fragrances, or deposition fragrances, and mixtures thereof.

9. The composition of claim 1 wherein said cross-linking ions comprise boron ions.

10. The composition of claim 9, wherein said boron ions are derived from at least one of Borax, sodium tetraborate, disodium tetraboratepentahydrate, disodium tetraborate decahydrate, sodium metaborate, and sodium perborate.

11. The composition of claim 1, wherein said cross-linking ions comprise persulfate ions.

12. The composition of claim 11, wherein said persulfate ions are derived from at least one of alkali peroxymonosulfate, alkali peroxydisulfate, and ammonium peroxydisulfate.

13. A method for the preparation of fragrance-containing microcapsules which are stable in a composition having a water phase and which encapsulate a non-solvent for said water phase, said method comprising the steps of:
 (a) providing an aqueous suspension of polyvinyl alcohol having a solids content within the range of about 3 to about 25% by weight;
 (b) combining said aqueous suspension of step (a) with at least one emulsifiable fragrance component under sufficient applied shear and for a time sufficient to obtain a stable emulsion of said at least one emulsifiable fragrance component in said aqueous suspension of polyvinyl alcohol; and
 (c) subsequently adding a source of boron or persulfate ions to said emulsion of step (b) in an amount sufficient to crosslink said polyvinyl alcohol to obtain an aqueous mixture of fragrance-containing microcapsules.

14. The method of claim 13, wherein said solids content of said polyvinyl alcohol in said aqueous solution in step (a) is about 4 to about 25% by weight.

15. The method of claim 13, wherein said source of boron ions is selected from the group consisting of Borax, sodium tetraborate, disodium tetraboratepentahydrate, disodium tetraborate decahydrate, sodium metaborate, and sodium perborate.

16. The method of claim 13, wherein said source of persulfate ions is selected from the group consisting of alkali peroxymonosulfate, alkali peroxydisulfate, and ammonium peroxydisulfate.

17. The method of claim 13, wherein said source of boron or persulfate ions is present in an amount of from about 0.1 to about 3% by weight.

18. The method of claim 13, wherein said at least one fragrance component is selected from the group consisting of essential oils, flash fragrances, sustained release fragrances, or deposition fragrances.

19. The method of claim 13, wherein said at least one fragrance component is present in an amount in the range of about 50 to about 95% by weight.

20. The method of claim 13, wherein said cross-linking ions comprise boron ions.

21. The method of claim 13, wherein said cross-linking ions comprise persulfate ions.

22. A method of delivering a fragrance to a substrate, comprising applying to said substrate an aqueous composition comprised of a water phase and fragrance-containing, boron or persulfate ion-crosslinked, polyvinyl alcohol microcapsules, said microcapsules being susceptible to disintegration in the absence of the application of crushing force upon drying of said composition subsequent to application of said composition to said substrate, said microcapsules being stable in water, and encapsulating a non-solvent for said water phase.

23. The method of claim 22, wherein said microcapsules contain a fragrant oil as a core material.

24. The method of claim 22, wherein said boron ions are derived from at least one of, Borax, sodium tetraborate, disodium tetraboratepentahydrate, disodium tetraborate decahydrate, sodium metaborate, and sodium perborate.

25. The method of claim 22, wherein said persulfate ions are derived from at least one of alkali peroxymonosulfate, alkali peroxydisulfate, and ammonium peroxydisulfate.

26. The method of claim 22, wherein said fragrance is selected from the group consisting of essential oils, flash fragrances, sustained release fragrances, or deposition fragrances, and mixtures thereof.

27. The method of claim 22, wherein said composition comprises a fabric care composition, a personal care composition, or a cleaning composition.

28. The method of claim 27, wherein said composition comprises hair shampoo, hair conditioner, dish detergent, laundry conditioner, fabric softener, hair or body rinse, body wash, skin cream, or laundry detergent.

29. The method of claim 22, wherein said cross-linking ions comprise boron ions.

30. The method of claim 22, wherein said cross-linking ions comprise persulfate ions.

31. A method of cleaning a substrate wherein a cleaning solution is applied to a substrate to be cleaned, wherein said cleaning solution comprises an aqueous cleaning composition comprised of a water phase and fragrance-containing, boron or persulfate ion-crosslinked, polyvinyl alcohol microcapsules together with an effective amount of at least one cleaning component, said microcapsules being stable in water, and encapsulating a non-solvent for the water phase.

32. The method of claim 31, wherein said microcapsules contain a fragrant oil as a core material.

33. The method of claim 31, wherein said boron ions are derived from at least one of Borax, sodium tetraborate, disodium tetraborate pentahydrate, disodium tetraborate decahydrate, sodium metaborate and sodium perborate.

34. The method of claim 31, wherein said persulfate ions are derived from at least one of alkali peroxymonosulfate, alkali peroxydisulfate, and ammonium peroxydisulfate.

35. The method of claim 31, wherein said fragrance is selected from the group consisting of flash fragrances, sustained release fragrances or deposition fragrances, and mixtures thereof.

36. The method of claim 31, wherein said cross-linking ions comprise boron ions.

37. The method of claim 31 wherein said cross-linking ions comprise persulfate ions.

* * * * *